Figure 1:
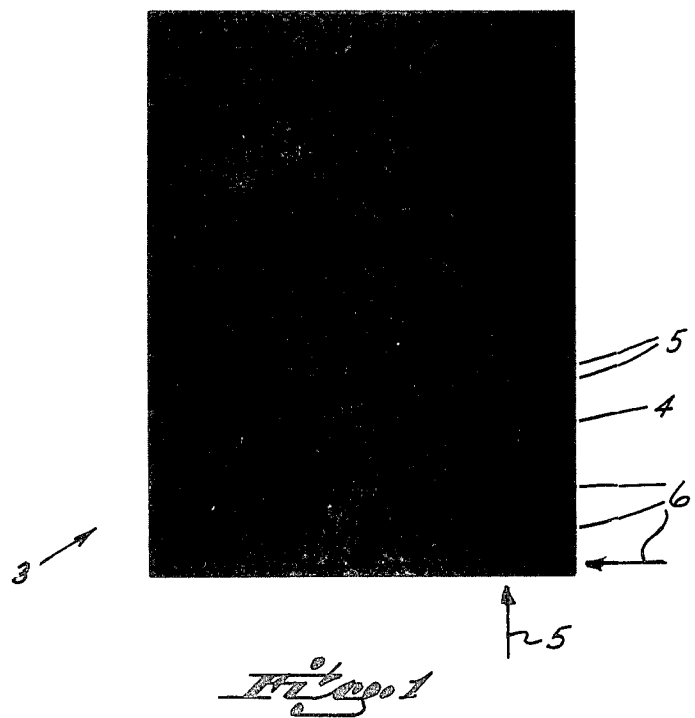

United States Patent [19]

Byrne et al.

[11] 4,376,147

[45] Mar. 8, 1983

[54] PLASTIC FILM HAVING A MATTE FINISH

[75] Inventors: Robert E. Byrne; Leopoldo V. Cancio; Arthur J. Raffel; Pai-Chuan Wu, all of Cincinnati, Ohio

[73] Assignee: Clopay Corporation, Cincinnati, Ohio

[21] Appl. No.: 298,346

[22] Filed: Aug. 31, 1981

[51] Int. Cl.³ .......................... B32B 1/00; B32B 3/30
[52] U.S. Cl. .................................. 428/167; 428/156; 428/179; 428/220; 428/500
[58] Field of Search ............... 428/167, 156, 179, 500; 264/284, 293

[56] References Cited

U.S. PATENT DOCUMENTS 2,660,757 12/1953 Smith et al. .................... 428/156
3,484,835 3/1968 Trounstine et al. .
3,911,187 10/1975 Raley ............................. 428/156

Primary Examiner—Paul J. Thibodeau
Attorney, Agent, or Firm—Wood, Herron & Evans

[57] ABSTRACT

A plastic film having a matte finish embossed on its surface is provided. The matte plastic film has excellent winding characteristics without edge curl, extremely low gloss even on both sides and good tape adhesion properties, among other advantages, which make it especially suitable for use in articles such as disposable diapers.

8 Claims, 2 Drawing Figures

PLASTIC FILM HAVING A MATTE FINISH

BACKGROUND OF THE INVENTION

Beginning several decades ago, plastic film began to achieve wide spread use in the fabrication of many useful articles, quite often as a replacement for woven fabrics. Early in the development of plastic film as a substitute for woven fabrics, patterns were created by imposing the image of a woven fabric into a film during the process of making the film. Wire screens, along with other mechanical implements, were later employed to create plastic films having various designs. As technology developed, metal rolls having engraved patterns were employed in the production of embossed plastic films which would simulate various designs. During this period of time, the person of ordinary skill in the art who made useful articles from plastic film, typically disposable diapers, covers, water repellant clothing, and the like, worked with the film on machinery and observed or studied its characteristics. Refinements or adjustments in the machinery as well as the material took place in order to produce useful articles from such embossed plastic films on high speed production machinery.

U.S. Pat. No. 3,484,835 which issued in 1969 is directed to a plastic film embossed with a pattern simulating a woven taffeta design and the film had especially desirable characteristics of edge curl resistance during machine processing into useful articles. Embossed plastic film disclosed in the patent offered significant improvements over the earlier taffeta design which existed in the prior art. The embossed plastic film having edge curl resistance was characterized by a series of bosses and channel-like areas, spaced apart by about 10 mils with the bosses protruding to a height within the range of about 3 to 4 mils and, on the opposite side, a series of depressed areas and ridges were created underlying the bosses and channel-like areas.

The simulated taffeta design disclosed by the above patent is only an example of one of many different designs created and employed by film fabricators in their effort to simulate woven fabrics or achieve other various visual appearances and physical properties which were advantageous from a manufacturing or consumer standpoint. Another one of such many designs is referred to in the art as a matte finish. A matte finish has heretofore been characterized by a rather dull finish on a plastic film with no visually perceptible pattern. Matte finishes have been produced in films by the employment of sand-blasted embossing rollers. With the advancement of technology including new formulations in polymer compositions of the polyolefin type, particularly polyethylene, polypropylene and polybutadiene, the problem of handling various films has become complex. While there is a considerable amount of knowledge available to a person of skill in this art, behaviors of polymers, or their properties under various physical conditions, such as machine stress and other conditions, are not readily understood. One might say that the plastic film technology is, indeed, more of an art than a science and experience has proven that problems in this area of the art are not as easily understood or solved owing to the unknown factors in handling such polymeric compositions under machine stress either in the manufacture or fabrication of such polymers into useful articles.

In connection with matte films, a number of problems exist, particularly the difficulty in achieving gloss control and satisfactory winding characteristics as the matte film is being handled and wound at high speeds on machinery. These problems are further complicated by the desirability to obtain other balanced characteristics in matte film such as good tape adhesion values, soft or cloth-like hand, low coefficient of friction properties, among other advantages. Furthermore, the problems associated with lack of machineability in currently available matte films have attempted to be minimized by improvements in equipment, such as the use of oscillators during winding in order to improve the otherwise undesirable matte film roll contouring characteristics. Against this background of prior art, it is evident that further improvements in matte film are needed.

SUMMARY OF THE INVENTION

This invention is directed to an embossed thermoplastic polyolefin film simulating a matte finish having excellent winding characteristics without edge curl, extremely low gloss even on both sides and good tape adhesion values, among other advantages, heretofore unachieved in prior art matte films. The thermoplastic films of this invention are relatively thin, particularly on the order of about 0.5 to about 1.5 mils. The film which has been found to provide the desired two-sided matte finish has an embossed depth on the order of about 0.5 to about 2.5 mils wherein the embossed pattern comprises embossed lines or channel-like areas which are parallel to the free lengthwise edges of the film. The parallel lengthwise lines or channel-like areas are intersected by transverse embossed lines or channel-like areas at such spacing so as to provide a generally rectangular pattern. Such parallel and transverse lines number within the range of about 150 to about 300 lines per inch. It is not essential for the transverse lines to perpendicularly intersect the parallel lengthwise embossed lines. In a preferred form of the invention, however, an overall generally rectangular pattern is achieved by the transverse lines being spaced apart at regular intervals to form a network of generally rectangular-shaped channels or lines separating raised boss areas on one side of the film, with underlying ribs or depressed areas on the opposite side of the film.

The matte film of this invention has been found to possess excellent roll contouring characteristics whereby the film may be handled on high speed machinery and it can be wound very flat. Even oscillating equipment otherwise necessarily used with previously known matte films may be avoided. In addition, the machine handling characteristics are further characterized by a lack of edge curl under machine stress. Very importantly, the overall matte finish is extremely low in gloss even on both sides and tape adhesion values are achieved which render the film particularly suitable for fabrication into useful articles such as disposable diapers where such adhesion values are needed. The embossed matte pattern may be referred to as a "micro-emboss", but one does not detect any pattern as such in the film. It simply appears to the unaided eye as a very dull surface. Also, the pattern imparts to the film a soft or cloth-like hand and low coefficient of friction properties without the addition, for instance, of slip agents. Thus, the matte design of this invention achieves a balance of the physical properties in the film heretofore unachieved in known matte films.

The matte film is made from suitable plastic materials, preferably of the thermoplastic polyolefin type and particularly polyethylene, polypropylene, polybutadiene, copolymers of such polyolefins such as ethylene vinyl acetate copolymers, or modified polyolefin polymers such as polyethylene or polypropylene modified with conventional fillers, stabilizers, additives and the like. As mentioned, the thickness of the films are on the order of about 0.5 to about 1.5 mils. A preferred polyolefin film is a low to medium density polyethylene. These plastic films can be embossed with the design of this invention according to any one of a number of well known techniques. A preferred method involves the introduction of thermoplastic material in a plastic state between usually a steel embossing roll and a smooth resilient roll or rubber roll which form a nip for embossing film. These techniques are considered conventional and are embodied herein by reference.

Figure 2:
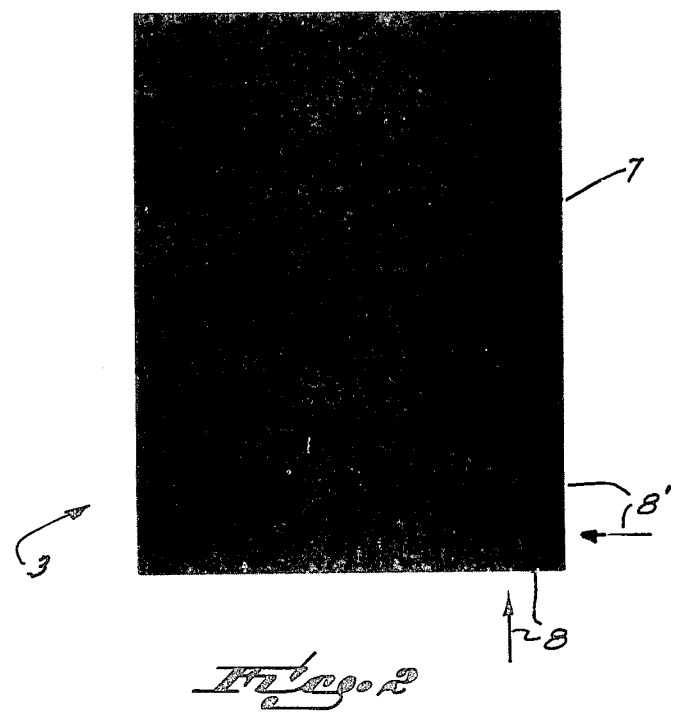
Figure 1:
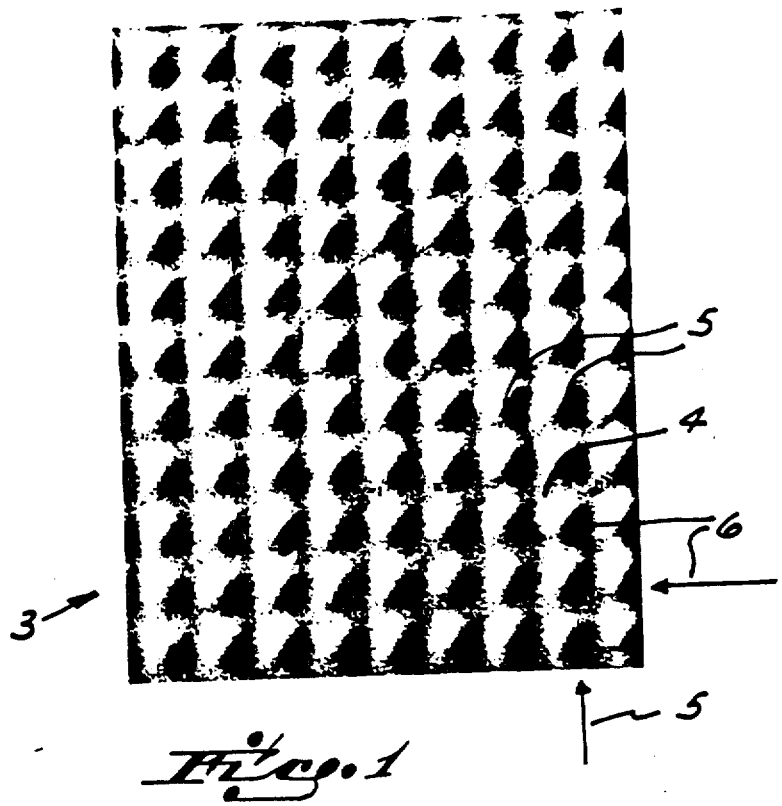
Figure 2:
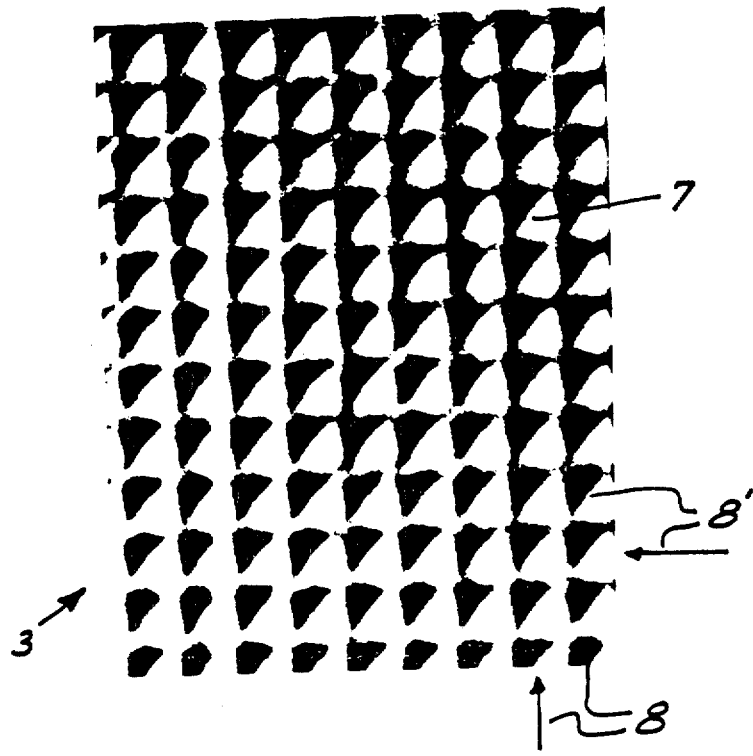

The invention will be further understood with reference to the drawing in which:

FIG. 1 is a magnified photographic top (rubber roll side) view of the matte film design of this invention and FIG. 2 is a magnified photographic view of the underside (metal embossing roll side) of the film of FIG. 1.

With reference to the photographs of FIGS. 1 and 2, a polyethylene film 3 is shown having a thickness in the range of about 0.5 to about 1.5 mils, more particularly about 1 mil. Under 45× magnification, the top view of plastic film looks like little bumps or bosses 4 which are separated by embossed lines 5 (or channel-like areas) substantially parallel to one another and to the free edges (not shown) of the film. Intersecting the parallel embossed lines 5 are a series of transverse embossed lines 6 (or channel-like areas). The intersecting embossed lines 5 and 6 thus surround a series of raised bosses 4 on the top side of the film. On the opposite underside side of the film in FIG. 2, there are a corresponding series of depressed areas 7 enclosed by substantially perpendicularly intersecting longitudinal and lateral ridges 8, 8'. Similarly, the bosses 4 in the top side of the film overlie the depressed areas 7 and the channel-like areas 5 and 6 overlie the underside ridges 8, 8'. The embossed lines or channel-like areas, as well as the underlying ridges, number about 165 per inch.

As developed above, in order to obtain the desired matte surface finish, it is essential that the film have embossed lines parallel and transverse to the lengthwise free edges of the film numbering within the range of about 150 to about 300 lines per inch and having an embossed depth of about 0.5 to about 2.5 mils. The "embossed depth" is determined by (a) measuring the average overall cross-sectional thickness of film from the top side of the bosses on the top side to the opposite outermost ridges on the underside and (b) measuring the average film thickness and subtracting (a) from (b). This measurement is made with a standard 1" micrometer in a manner known to those of skill in the art, for instance, among other techniques. This embossed pattern provides the desired matte visual effect with no observable pattern to the unaided eye. As developed above, the transverse lines are preferably similarly dimensioned, i.e., numbering within the range of about 150 to about 300 lines per inch such that an overall network of lines or channels is provided surrounding the bosses. This pattern enables the obtainment of excellent roll contouring without edge curling and a very low gloss on both sides with desired tape adhesion values, among other features, as developed above. The transverse lines, however, need not be exactly perpendicular to the lines which run parallel to the free edges of the film. It is important, however, that the transverse lines be spaced apart to form an overall network such that the surface of the film is imparted with the design which gives the visual matte appearance and yet has the desired flat winding characteristics along with edge curl resistance. Of course, the embossed lines at their intersections, depending upon the uniformity of embossed pattern, may tend to interrupt one another such that different surface levels may be obtained from one end of a channel or line to the other end.

With further reference to the photographs of the drawings, it will be appreciated by one of ordinary skill in this art that channel-like areas or embossed lines are formed in the surface such that there are smooth transitions between bosses and channel-like areas on the top side of the film. The same is true for ridges and depressions on the underside of the film. On the underside of the film it may be observed that counterpart ridges extend at regular intervals across the entire underside of the film to define a network of ridges which integrally boarder the depressions. When the embossed lines tend to be less than about 150 lines per inch, depending upon the embossed depth, the matte finish may tend to be destroyed and, on the other hand, above about 2.5 mils in embossed depth, the pattern may tend to be observable. Therefore, it may be appreciated that the embossed depth must be balanced within the range of about 0.5 to about 2.5 mils wherein the embossed pattern of embossed lines is within the range of about 150 to about 300 lines per inch in order for the matte finish and physical properties to be achieved.

The embossed matte pattern is formed, for example, by embossing a plastic film with a system of embossing rolls. One of the rolls is a steel roll whose surface is engraved with a pattern of either protrusions or pins, and which is commonly referred to as a male embossing roll. On the other hand, a female pattern may be engraved into the roll by a series of depressions. A female pattern is created, for instance, by engraving the depressions or "pins down" into the steel roll to a depth of approximately 0.001 to 0.003 inch. The steel tool engraved pattern will substantially correspond to the underside of the embossed film, it being appreciated that exact conformance will usually not be achieved. The other roll of the embossing system is a rubber roll into which the steel roll pattern is impressed during the formation of the film by the usual technique of slot-die extrusion. The speed of the rubber and steel rolls is maintained to permit continuous embossing of the film for subsequent take-up on a wind-up roller.

In a preferred form of the invention, a low to medium density polyethylene is formed into a matte film by a slot-die extrusion means. For example, the low to medium denisty polyethylene material is heated to a temperature of about 300°–350° F. and then introduced in a web form through a slot into the nip of the steel and rubber roll system referred to above. Plastic material, upon being introduced between the nip of the rolls, is film-formed and at the same time textured with the embossed pattern of the steel embossing roll. Under suitable embossing pressure of for instance about 25–30 psi a thin film having the embossed design may be produced. In achieving the preferred film thickness of between about 0.5 to about 1.5 mils, along with the necessary embossed depth of about 0.5 to about 2.5 mils, conditions are controlled in a manner well within the skill of those knowledgeable in the art of producing embossed films with an understanding of the disclosure of this invention. The factors which are considered may be varied depending upon the plastic material used and the characteristics to be obtained in the resultant film. Thus, process conditions which are obviously controlled to produce embossed film include temperature, pressure exerted between the nip of the embossing roller system, the depth of the engraved design on the steel roll and the hardness of the resilient material of the rubber roll. Furthermore, the matte pattern may be imparted to the plastic film under normal or ambient conditions by means of post embossing with certain polymers such as polybutadiene. Typical properties of a low to medium density polyethylene matte film that are achieved in accordance with the principles of this invention, where the embossed lines numbered about 250 per inch, are demonstrated by the Table below. The polyethylene in Samples A and B had a melt index of about 1.8 and a density of about 0.926.

TABLE

|  | SAMPLE A | SAMPLE B |
| --- | --- | --- |
| Gram Weight (g/240 in$^2$) | 3.85 | 3.80 |
| Ultimate Tensile MD (g/in) CD | 1920 1195 | 1930 1170 |
| Elongation at Break MD (%) CD | 345 810 | 380 870 |
| MD Tensile at 25% Elongation (g/in) | 690 | 790 |
| Impact (ft-#) | 1.25 | 1.23 |
| C.O.F.$^3$ (metal side/metal side) | 0.8–0.9 | 0.6–0.7 |
| Gloss (metal side) (45° head) (rubber side) | 3–4 5–6 | 3–4 5–6 |
| Tape Adhesion Force (grams) | 827 | 884 |

$^1$MD = machine direction
$^2$CD = cross direction
$^3$C.O.F. = coefficient of friction With reference to the above Table and the detailed description, the embossed plastic film of this invention is provided with a matte finish of very low gloss on either side and in which no pattern is observable with the unaided eye. The product exemplified in the Table has a soft or cloth-like hand feel. Upon winding, the product has excellent roll contouring characteristics without edge curl or the requirement of an oscillation of the winder in the winding process. In addition, good coefficient of friction properties are obtained without the addition of slip agents. Other advantages, such as good tape adhesion, are also obtained.

In view of the above detailed description of the invention, it will be apparent to a person of ordinary skill in this art that variations of the parameters of this invention may be employed and the desired results may still be achieved.

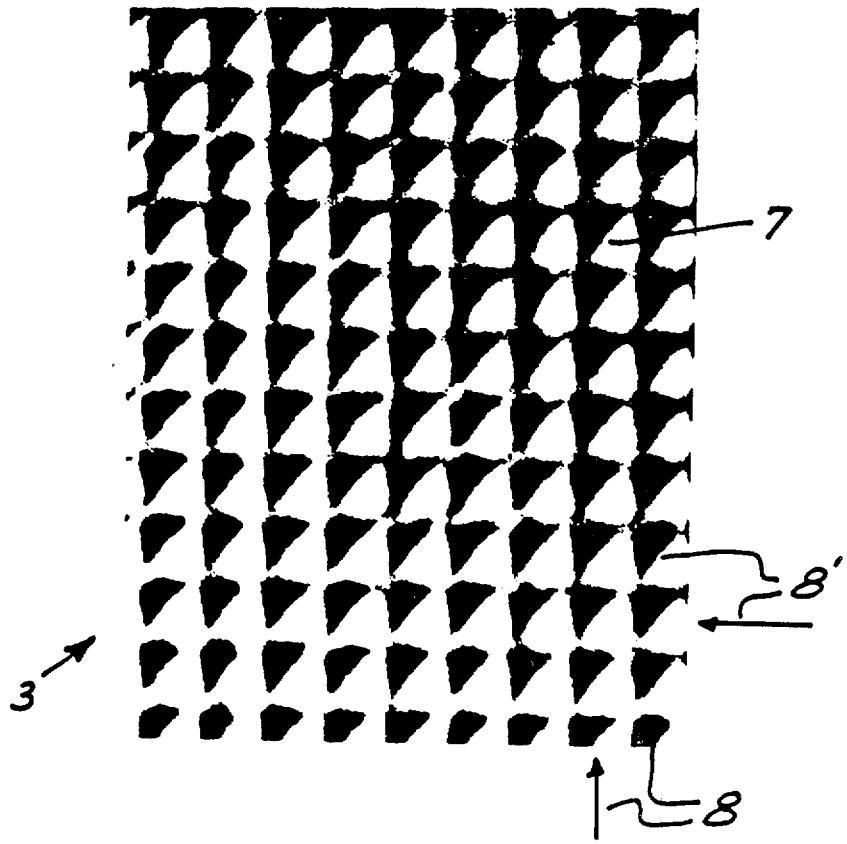

We claim:

1. An embossed thermoplastic polyolefin film having an embossed matte pattern which is undetectable to the unaided eye and imparts a dull surface to the film, said film having a thickness within the range of about 0.5 to about 1.5 mils and an embossed depth of about 0.5 to about 2.5 mils wherein the embossed pattern comprises a series of embossed lines parallel to free lengthwise edges of the film and a series of embossed transverse lines intersecting said parallel lines to provide an overall general network of said lines surrounding raised bosses on one side of the film, wherein said bosses and said lines overlie on the opposite side of said film corresponding depressions and ridges, said embossed lines numbering within the range of about 150 to 300 lines per inch, said film having excellent winding characteristics and edge curl resistance.

2. The embossed film of claim 1 wherein said polyolefin is selected from the group consisting of polyethylene, polypropylene, and copolymers thereof.

3. The embossed film of claim 1 wherein said transverse lines are perpendicular to said parallel lines.

4. The embossed film of claim 1 wherein said transverse and parallel lines are spaced apart substantially equally to form an overall generally rectangular network.

5. The embossed film of claim 4 wherein said lines number about 250 lines per inch.

6. An embossed thermoplastic polyolefin film having an embossed matte pattern which is undetectable to the unaided eye and imparts a dull surface to the film, said polyolefin film selected from the group consisting of polyethylene, polypropylene, polybutadiene and copolymers thereof, said film having a thickness within the range of about 0.5 to about 1.5 mils and an embossed depth of about 0.5 to about 2.5 mils wherein the embossed pattern comprises a series of embossed lines parallel to free lengthwise edges of the film and a series of embossed transverse lines perpendicularly intersecting said parallel lines to provide an overall rectangular network of said lines surrounding raised bosses on one side of the film, wherein said bosses and said lines overlie on the opposite side of said film corresponding depressions and ridges, said embossed lines numbering within the range of about 150 to 300 lines per inch, said film having excellent winding characteristics and edge curl resistance.

7. The embossed film of claim 6 wherein said film has low gloss on both sides.

8. The embossed film of claim 6 having a combination of tape adhesion, low gloss and coefficient of friction properties on said raised boss side of the film especially adapted for diaper applications.

* * * * *

UNITED STATES PATENT AND TRADEMARK OFFICE
CERTIFICATE OF CORRECTION

PATENT NO. : 4,376,147
DATED : March 8, 1983
INVENTOR(S) : Robert E. Byrne, et al It is certified that error appears in the above-identified patent and that said Letters Patent is hereby corrected as shown below:

The title page and sheet 1 of the drawings containing Figures 1 and 2 should appear as shown on the attached sheets.

Signed and Sealed this

Seventh Day of August 1984

[SEAL]

Attest:

GERALD J. MOSSINGHOFF

*Attesting Officer*    *Commissioner of Patents and Trademarks*

United States Patent [19]
Byrne et al.

[11] 4,376,147
[45] Mar. 8, 1983

[54] PLASTIC FILM HAVING A MATTE FINISH

[75] Inventors: Robert E. Byrne; Leopoldo V. Cancio; Arthur J. Raffel; Pai-Chuan Wu, all of Cincinnati, Ohio

[73] Assignee: Clopay Corporation, Cincinnati, Ohio

[21] Appl. No.: 298,346

[22] Filed: Aug. 31, 1981

[51] Int. Cl.³ .......................... B32B 1/00; B32B 3/30
[52] U.S. Cl. .................................. 428/167; 428/156; 428/179; 428/220; 428/500
[58] Field of Search ............... 428/167, 156, 179, 500; 264/284, 293

[56] References Cited
U.S. PATENT DOCUMENTS

| | | |
|---|---|---|
| 2,660,757 | 12/1953 | Smith et al. .................... 428/156 |
| 3,484,835 | 3/1968 | Trounstine et al. |
| 3,911,187 | 10/1975 | Raley .................... 428/156 |

Primary Examiner—Paul J. Thibodeau
Attorney, Agent, or Firm—Wood, Herron & Evans

[57] ABSTRACT

A plastic film having a matte finish embossed on its surface is provided. The matte plastic film has excellent winding characteristics without edge curl, extremely low gloss even on both sides and good tape adhesion properties, among other advantages, which make it especially suitable for use in articles such as disposable diapers.

8 Claims, 2 Drawing Figures